United States Patent [19]

Deysarkar et al.

[11] Patent Number: 4,648,263

[45] Date of Patent: Mar. 10, 1987

[54] SUPPORT AND CENTERING ATTACHMENTS FOR SENSITIVE VISCOMETERS

[75] Inventors: Asoke K. Deysarkar, Burwell; James D. Allen, Woodlands, both of Tex.

[73] Assignee: Pennzoil Company, Houston, Tex.

[21] Appl. No.: 806,774

[22] Filed: Dec. 9, 1985

[51] Int. Cl.⁴ ............................................. G01N 11/14
[52] U.S. Cl. ........................................................ 73/59
[58] Field of Search ............................................. 73/59

[56] References Cited

U.S. PATENT DOCUMENTS

| | | |
|---|---|---|
| 2,573,505 | 10/1951 | Steffens . |
| 2,679,750 | 6/1954 | Brookfield . |
| 2,957,339 | 10/1960 | Penny et al. ............................. 73/59 |
| 3,572,086 | 3/1971 | Johnston ................................. 73/59 |
| 3,611,789 | 10/1971 | Lopas ..................................... 73/59 |
| 3,886,789 | 6/1975 | Brookfield . |
| 3,935,726 | 2/1976 | Heinz . |
| 4,062,225 | 12/1977 | Murphy, Jr. et al. . |
| 4,175,425 | 11/1979 | Brookfield . |
| 4,214,475 | 7/1980 | Carter et al. . |
| 4,299,118 | 11/1981 | Gau et al. . |
| 4,448,061 | 5/1984 | Brookfield . |

Primary Examiner—Jerry W. Myracle
Assistant Examiner—Joseph W. Roskos
Attorney, Agent, or Firm—Lowe, Price, LeBlanc, Becker & Shur

[57] ABSTRACT

A cylindrical support and centering device for a sensitive viscometer comprises a hollow cylindrical support member open at opposite ends. The viscometer is supported on the upper end with its cylindrical pivot housing slip-fitted into the upper end in snug contact with an inner cylindrical surface of the support. The pivot housing either rests against an annular stop surface formed below the cylindrical surface or is supported by contact of the viscometer with the upper end. The lower end of the support is dimensioned to snugly engage the outer cylindrical surface of the stator so that the longitudinal axis of the stator is coaxial with the longitudinal axis of the rotor for precise centering.

16 Claims, 4 Drawing Figures

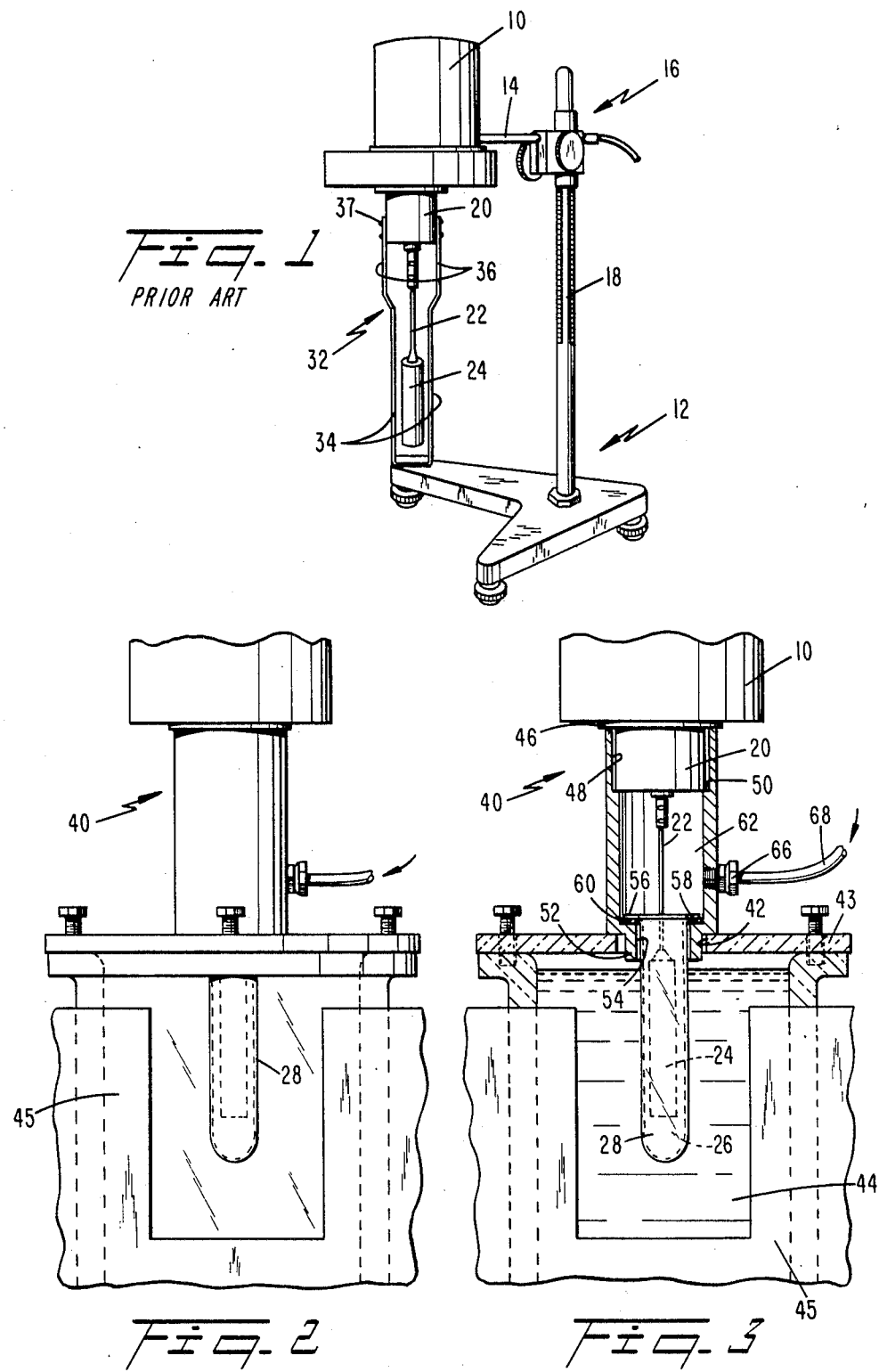

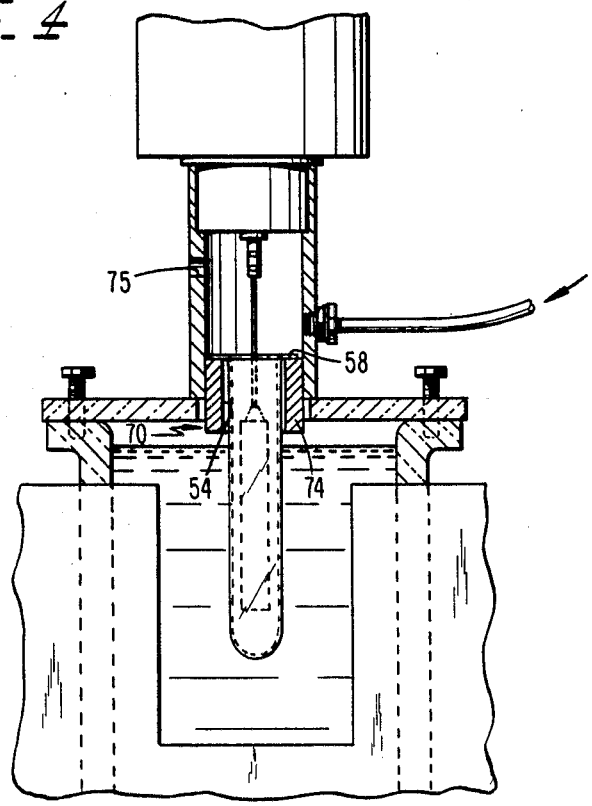

SUPPORT AND CENTERING ATTACHMENTS FOR SENSITIVE VISCOMETERS

TECHNICAL FIELD

The present invention relates generally to viscometers and, more particularly, to attachments for centering with respect to each other various rotational parts within the viscometer to improve accuracy in measurement of viscosity.

BACKGROUND ART

Viscometers are widely used in the oil and other industries to measure the flow properties and especially the low temperature flow properties of various lubricants. One known instrument for measuring such properties is the Brookfield Digital Viscometer manufactured by Brookfield Engineering Laboratories, Inc. of Stoughton, Mass. 02072. This type of viscometer measures fluid viscosity by employing the principle of rotational viscometry, i.e., measurement of viscosity by sensing the torque required to rotate a spindle at constant speed while immersed in a sample fluid. The torque is proportional to the viscous drag on the immersed spindle, and thus to fluid viscosity.

FIG. 1 is an illustration of a commercial viscometer 10 which is similar to the Brookfield Digital Viscometer mentioned above. Viscometer 10 is mounted on a stand 12 with a horizontal arm 14 held by clamp 16. The clamp 16 may be vertically adjustable along an upright support 18. Viscometer 10 includes a cylindrical pivot housing 20 from which depends a shaft 22 that may support a cylindrical metallic rotor 24 or the like. The viscometer 10 rotates the rotor 24 through shaft 22 while measuring the torque or drag transmitted through the shaft by virtue of resistance encountered by the rotor immersed within a viscous fluid sample. The sample is contained within a stationary container or stator which has an inner cylindrical side wall.

To obtain a precise indication of absolute viscosity, especially for non-Newtonian fluids, it is important that the outer cylindrical wall of the rotor be equispaced from the inside cylindrical surface of the stator. With known spacing, it is possible to calculate the rate of shear of the sample fluid to obtain absolute viscosity measurements from relative viscosity. However, if spacing between rotor 24 and the stator cannot be precisely determined, i.e., if these parts cannot be centered with respect to each other, then accuracy in viscosity determination is impaired.

In the prior art viscometer disclosed supra, centering the stator and rotor is made by requiring the operator to move the stator until the operator feels that the rotor is centered within the stator. To assist in this visual alignment, viscometer 10 further includes a guard leg 32 in the form of a U-shaped member having a pair of lower straight sections 34 formed parallel to each other. These straight sections 34 extend along and are equispaced from the rotor. These straight sections 34 include upper parallel straight sections 36 connected to pivot housing 20 with screws 37. The straight sections 34, by virtue of being located between the rotor 24 and the inner cylindrical surface of the stator, assist the operator in visually centering the rotor within the stator. However, centering of these parts relative to each other by the operator still remains subjective and is dependent upon the operator's skill level. Thus, non-accurate, non-reproducible viscosity determinations are likely to occur with prior art viscometer 10.

It is accordingly one object of the present invention to provide a centering and support device which supports both the glass stator tube as well as the viscometer and rotor combination to obtain precise and consistently reproducible centering between the stator and rotor.

Another object of the invention is to provide a device providing stable support for the viscometer and rotor combination and which further provides for automatic centering of the viscometer so that the rotor is suspended perpendicular to the pivot housing.

Still another object is to provide a cylindrical support and centering device allowing the operator to calculate absolute viscosity of non-Newtonian fluids.

Yet a further object is to provide a support and centering device and method suitable for conducting viscosity measurements of low temperature fluids by maintaining an inert atmosphere above the fluid sample surface to prevent ice formation.

DISCLOSURE OF THE INVENTION

A device is disclosed for supporting a sensitive viscometer above a cylindrical stator containing a predetermined quantity of fluid. The fluid viscosity is measured by a cylindrical rotor suspended from a pivot housing fixed to the lower end of the viscometer and centered within the fluid by the device. The rotor, being rotatable about its longitudinal axis by the viscometer, cooperates with the stator and fluid to create drag related to viscosity. The device comprises a hollow support member having interior first surfaces for supporting the pivot housing within the member so that the housing is radially and axially immovable. The device further includes second interior surfaces for supporting the stator within the member so that the stator is radially and axially immovable and the longitudinal axis of the stator is in coaxial alignment with the longitudinal axis of the rotor. The first and second surfaces are axially spaced from each otherwithin the support member so that the rotor is immersed within the fluid.

More specifically, the hollow support member has an open upper end and an upper interior surface shaped to correspond and snugly engage the exterior surface of the pivot housing to prevent radial movement. The housing may be axially fixed in position by contact between a lower surface thereof and an upwardly directed annular stop surface formed below the upper interior surface, or by contact between the lower part of the viscometer resting against the upper end of the support member. The support member further includes a lower interior surface which may be cylindrical and in snug contact with the exterior corresponding surface of the stator. The stator is axially fixed within the support member preferably by means of a second annular stop surface supporting an annular lip formed on the exterior surface of the stator.

In accordance with one embodiment of the invention, the stator projects below the support member. The lower end of the support member is fitted within a hole formed in a horizontal support plate extending above a support surface. The stator projects through the lower end and is maintained in suspended position above the support surface by the support member resting upon the plate.

The support member of the invention is ideally suited for use in conducting low temperature viscosity measurements in combination with a temperature controller unit containing a reservoir filled with a temperature controlled bath. In this embodiment, the support plate covers the bath and the hole formed therein is situated above the bath so that the stator is immersed within the reservoir. The pivot housing and upper end of the stator jointly define an interior region within the support member that preferably contains an inert atmosphere for preventing formation of ice on the surface of fluid within the stator. The inert atmosphere is preferably nitrogen injected into the sealed region through a threaded fitting in a side wall of the support member connected to tubing supplying the nitrogen. A vent formed in the side wall generally opposite the threaded fitting may be provided to prevent pressure build-up of inert gas within the interior region.

In accordance with one embodiment of the invention, the stator is axially immovably supported within the support member by a cylindrical member having an exterior cylindrical surface, an upper portion of which is fixed to the lower portion of the interior surface of the hollow support member. The upper edge of the cylindrical member extends radially inwardly from the side wall of the hollow support member to define the second annular stop surface supporting the annular lip of the stator. In an alternate embodiment, the second annular stop surface is formed integrally with the hollow support member having a lower end of reduced diameter relative to the upwardly extending side wall of the hollow support.

In the preferred embodiment, the cylindrical member is preferably formed of a material, such as Teflon ®, that prevents breakage of the delicate stator when it is initially inserted into the device. This material also performs a sealing function when the device is used with a temperature controller unit to seal the interior region from ambient atmosphere.

In the alternate embodiment, a gasket may be disposed between the annular lip of the stator and the lower second stop surface of the support member. The gasket, being preferably an elastomeric material or Teflon ®, prevents breakage of the delicate stator when it is initially inserted into the device. When used in combination with the temperature controller unit, the gasket also assists in sealing the region from ambient atmosphere.

Still other objects and advantages of the present invention will become readily apparent to those skilled in this art from the following detailed description of the invention, wherein I have shown and described only the preferred embodiment of the invention, simply by way of illustration of the best mode contemplated by me of carrying out my invention. As will be realized, the invention is capable of modifications in various obvious respects, all without departing from the invention. Accordingly, the drawings and description are to be regarded as illustrative in nature and not as restrictive.

BRIEF DESCRIPTION OF THE DRAWING

FIG. 1 is a perspective view of a prior art viscometer and support stand therefor;

FIG. 2 is a side elevational view of a support and centering device in accordance with the present invention;

FIG. 3 is a cross-sectional view of the device depicted in FIG. 2; and

FIG. 4 is similar to FIG. 3 but showing a preferred embodiment of the present invention.

BEST MODE FOR CARRYING OUT THE INVENTION

Referring to FIGS. 2 and 3, support and centering device 40 is shown supporting the viscometer 10 of FIG. 1 with cylindrical rotor 24 precisely centered within stator 28. The device 40 may be mounted within an opening 42 formed in a top plate 43 that covers a reservoir containing a temperature controlled bath 44. The stator 28 is suspended within bath 44 by device 40. The reservoir may be formed within a commercially available temperature controller unit 45, only a part of which is shown, such as a model TSI 410 programmable liquid bath, manufactured by Siverso, rue du Hoc 76600 Le Havre, France. The unit 45 is employed for conducting low temperature viscosity measurements of fluid within stator 28. However, as will be seen more fully below, the device 40 is capable of use for conducting other viscosity measurements independent of a temperature controller unit.

Device 40, preferably aluminum, is a cylindrical support member open at opposite ends thereof. The upper end 46 is formed with an inner cylindrical surface 48 of constant diameter dimensioned to receive pivot housing 20 in slip-fitting snug contact. Viscometer 10 may be supported upon device 40 by contacting upper end 46 as depicted in FIG. 3, or by forming an annular, upwardly directed stop surface 50 along the lower end of surface 48 adapted to contact the lower end of pivot housing 20 (also shown in FIG. 3). In either case, it is preferable to form surface 48 so that it is capable of receiving the entire housing 20 in snug contact for maximum support.

The lower end 52 of device 40 is also formed with an inner cylindrical surface 54 dimensioned to receive and encircle an upper end of stator 28 in slip-fitting snug contact. The surfaces 48, 54 are formed concentric with respect to the longitudinal axis of device 40. Therefore, it will be appreciated that perfect centering of rotor 24 within stator 28 is achieved by simply slipping the stator through the upper end of the device until the annular lip 56 contacts the upwardly directed stop surface 58 formed above surface 54. Thereafter, pivot housing 20 is inserted into upper end 46. The stop surfaces are axially spaced from each other so that rotor 24 is perfectly centered and suspended within fluid sample 26 contained in stator 28.

In a preferred embodiment of the invention, FIG. 4, the surfaces 54, 58 are formed on a cylindrical member 70 preferably of constant internal and external diameter for simplicity in design. The upper portion 72 of exterior surface 74 of member 70 is immovably fixed to the lower end of the interior surface of device 40. In this preferred embodiment, device 40 has a straight cylindrical lower portion in comparison with the arrangement of FIG. 3.

The pivot housing 20 and stator 28 are usually formed with exterior cylindrical surfaces. However, it will be appreciated that surfaces 48, 54 may be machined or otherwise formed in other shapes to accommodate different exterior surfaces of the pivot housing and stator, still resulting in precise centering of the parts.

Because stator 28 is fitted into the lower end of device 40 by initially passing the stator through upper end 46, a gasket 60 is preferably placed upon lower stop surface 58 (FIG. 3) to cushion the annular lip as it is seated in position thereon. Since stator 28 is usually made of fragile glass, gasket 60 minimizes the likelihood of breakage. Gasket 60 is preferably made from either elastomeric material or foam and further serves to compensate for machining errors that may occur during formation of the lower stop in order to obtain precise centering of the stator and rotor. In the preferred FIG. 4 embodiment, however, gasket 60 may be eliminated by forming cylindrical member 70 from Teflon ® or like material.

As shown in FIGS. 3 and 4, the spacing of the upper and lowerstop surfaces 50,58 in the manner described above results in formation of an interior region 62 communicating with the interior of the stator through the open end thereof. When conducting low temperature viscosity measurements, it is preferable to inject an inert atmosphere (e.g., nitrogen) into the upper end of the stator to prevent ice formation on the surface of the fluid being measured. Device 40 advantageously facilitates injection of nitrogen into stator 28 by allowing injection to occur into region 62 through a fitting 66 and tubing 68 connected to a source of nitrogen (not shown). It will be further appreciated that gasket 60 (FIG. 3) or member 70 (FIG. 4) seals region 62 in cooperation with pivot housing 20 during low temperature testing to prevent ambient atmosphere from entering the stator. However, as depicted in FIG. 4, a vent 75 may be provided to prevent a pressure build-up of inert gas within interior region 62.

In accordance with the above disclosure, it will be appreciated that an important feature of the present invention is the ability to achieve automatic and precise centering of rotor 24 within stator 28 in a manner that is not dependent upon the skill of an operator. The upper and lower coaxial surfaces 48,54 of device 40 provide for automatic and precise self centering of the component parts so that test results can be easily duplicated to obtain accurate, reproducible vicosity determinations in seconds, regardless of the operator's skill level.

Although centering device 40 as illustrated requires that stator 28 project below the device, preferably for use in connection with low temperature viscosity measuring, it will be appreciated that device 40 can be employed in non-low temperature testing environments by supporting the device on an elevated plate 43 suitably mounted on support structure (not shown) allowing stator 28 to depend below the plate through opening 42 as described supra. Of course, it will be necessary to level the plate 43; however, this is easily and reliably accomplished using state of the art leveling equipment as is well known.

It will be further appreciated by those skilled in the art that device 40 can be employed without an elevated mounting plate 43 by forming the device with a side wall projecting downwardly from the lower cylindrical surface 54 so that the stator 28 is disposed entirely in the device. In this case, the lower end of device 40 would rest upon a suitable support surface that has been perfectly leveled as described supra.

The foregoing description of a preferred embodiment of the present invention has been presented for purposes of illustration and description. It is not intended to be exhaustive or to limit the invention to the precise form disclosed, and obviously many modifications and variations are possible, in light of the above teachings.

We claim:

1. A device for supporting a sensitive viscometer above a cylindrical stator containing a predetermined quantity of fluid, the viscosity of said fluid being measured by a cylindrical rotor suspended from a pivot housing fixed to the lower end of the viscometer and centered within the fluid by said device, said rotor being rotatable about its longitudinal axis by the viscometer and cooperating with said stator and fluid to create drag related to said vicosity, said device comprising a hollow support member havingan open upper end and upper interior surface shaped to correspond and snugly engage the exterior surface of said pivot housing; said viscometer projecting upwardly from substantially the upper end of said support member, first means for retaining said pivot housing in stationary position and snug contact with said upper interior surface; said support member further including a lower interior cylindrical surface in snug contact with the exterior cylindrical surface of said stator, and second means for retaining said stator in stationary position and snug contact with said lower cylindrical surface, said upper and lower surfaces being coaxial with each other to substantially precisely center the rotor within the stator.

2. The device of claim 1, wherein said first means includes said upper end of the support member lying in a common plane of said support member to support the viscometer.

3. The device of claim 1, further comprising a temperature controller unit containing a reservoir filled with a temperature controlled bath for conducting low temperature viscosity measurements of fluid contained within said stator; and means for supporting said support member on said unit with the stator projecting below said member and into the bath.

4. The device of claim 3, wherein said supporting means includes a plate mounted to cover said bath, said plate having a hole through which the stator is suspended within the bath, the lower end of the support member being disposed within the hole and being formed with an exterior shoulder defining a downwardly directed surface in contact with the periphery of the hole to support the viscometer on the plate.

5. A device for supporting a sensitive viscometer above a cylindrical stator containing a predetermined quantity of fluid, the viscosity of said fluid being measured by a cylindrical rotor suspended from a pivot housing fixed to the lower end of the viscometer and centered within the fluid by said device, said rotor being rotatable about its longitudinal axis by the viscometer and cooperating with said stator and fluid to create drag related to said viscosity, said device comprising a hollow support member having an open upper end and upper interior surface shaped to correspond and snugly engage the exterior surface of said pivot housing; first means for retaining said pivot housing in stationary position and snug contact with said upper interior surface; said support member further including a lower interior cylindrical surface in snug contact with the exterior cylindrical surface of said stator, and second means for retaining said stator in stationary position and snug contact with said lower cylindrical surface, said upper and lower surfaces being coaxial with each other to substantially precisely center the rotor within the stator, wherein said second means includes a second step formed between said lower cylindrical surface and a first step, said second step defining an upwardly directed nesting surface, said stator including an annular lip resting upon said nesting surface.

6. The device of claim 5, further including a gasket disposed between said nesting surface and lip to prevent breakage of said stator.

7. The device of claim 6, wherein said gasket is formed of elastomeric material.

8. A device for supporting a sensitive viscometer above a cylindrical stator containing a predetermined quantity of fluid, the viscosity of said fluid being measured by a cylindrical rotor suspended from a pivot housing fixed to the lower end of the viscometer and centered within the fluid by said device, said rotor being rotatable about its longitudinal axis by the viscometer and cooperating with said stator and fluid to create drag related to said viscosity, said device comprising a hollow support member having an open upper end and upper interior surface shaped to correspond and snugly engage the exterior surface of said pivot housing; first means for retaining said pivot housing in stationary position and snug contact with said upper interior surface; said support member further including a lower interior cylindrical surface in snug contact with the exterior cylindrical surface of said stator, and second means for retaining said stator in stationary position and snug contact with said lower cylindrical surface, said upper and lower surfaces being coaxial with each other to substantially precisely center the rotor within the stator, further comprising a temperature controller unit containing a reservoir filled with a temperature controlled bath for conducting low temperature viscosity measurements of fluid contained within said stator; and means for supporting said support member on said unit with the stator projecting below said member and into the bath, wherein said supporting means includes a plate mounted to cover said bath, said plate having a hole through which the stator is suspended within the bath, the lower end of the support member being disposed within the hole and being formed with an exterior shoulder defining a downwardly directed surface in contact with the periphery of the hole to support the viscometer on the plate, wherein the pivot housing engaged within the upper end of the support member and the stator engaged within the lower end of said support member define within said member a generally sealed region in communication with said fluid through the open end of the stator; and means for introducing an inert atmosphere into said sealed region to prevent formation of ice on the surface of fluid within the stator during low temperature viscosity measurements.

9. The device of claim 8, wherein a side wall of said support member surrounding said region includes an opening containing a threaded fitting connected to a tube supplying an inert gas to the region.

10. The device of claim 9, wherein said inert gas in nitrogen.

11. The device of claim 9, wherein said side wall includes a vent opening.

12. A device for supporting a sensitive viscometer above a cylindrical stator containing a predetermined quantity of fluid, the viscosity of said fluid being measured by a cylindrical rotor suspended from a pivot housing fixed to the lower end of the viscometer and centered within the fluid by said device, said rotor being rotatable about its longitudinal axis by the viscometer and cooperating with said stator and fluid to create dragrelated to said viscosity, said device comprising a hollhollow support member having interior first means for supporting the pivot housing with the member so that said housing is radially and axially immovable; and interior second means for supporting the stator within the member so that the stator is radially and axially immovable and the longitudinal axes of the stator and rotor are coaxially aligned with each other; said first and second means being axially spaced from each other within the support member so that the rotor is immersed within the fluid, wherein said second means includes a cylindrical member fixed to the interior surface of said hollow support member so that an upper edge of the cylindrical member projects radially inwardly from said support member to define a stop surface supporting an annular lip of the stator within the hollow support member.

13. The device of claim 12, wherein said cylindrical member is Teflon ® or like material.

14. A method of precisely centering with a support device a cylindrical rotor within a fluid filled stator for measuring viscosity of said fluid with a sensitive viscometer, said rotor depending from a pivot housing projecting below the viscometer; comprising the steps of:
   (a) positioning the stator so that an exterior periphery thereof contacts a first interior surface of the device and is securely held thereby within said device with the longitudinal axis of the stator in co-axial alignment with the longitudinal axis of the device; and
   (b) lowering the rotor into the stator until the periphery of the pivot housing snugly contacts a second surface of the device located above the first surface with the viscometer projecting upwardly from said second surface, said second surface positioning the rotor so that a longitudinal axis thereof is coaxially aligned and substantially precisely centered within the stator.

15. A device for supporting a sensitive vescometer above a cylindrical stator containing a predetermined quantity of fluid, the viscosity of said fluid being measured by a cylindrical rotor suspended from a pivot housing fixed to the lower end of the viscometer and centered within the fluid by said device, said rotor being rotatable about its longitudinal axis by the viscometer and cooperating with said stator and fluid to create drag related to said viscostiy, said device comprising a hollow support member having interior first means for supporting the pivot housing within the member so that said housing is radially and axially immovable; and interior second means for supporting the stator within the member so that the stator is radially and axially immovable and the longitudinal axes of the stator and rotor are coaxially aligned with each other; said first and second means being axially spaced from each ohter within the support member so that the rotor is immersed within the fluid, said viscometer projecting upwardly from substantially the upper end of said support member.

16. A device for supporting a sensitive viscometer above a cylindrical stator containing a predetermined quantity of fluid, the viscosity of said fluid being measured by a cylindrical rotor suspended from a pivot housing fixed to the lower end of the viscomter and centered within the fluid by said device, said rotor being rotatable about its longitudinal axis by the viscometer and cooperating with said stator and fluid to create drag related to said viscosity, said device comprising a hollow support member having an open upper end and upper interior surface shaped to correspond and snugly engage the exterior surface of said pivot housing; first means for retaining said pivot housing in stationary position and snug contact with said upper interior surface; said support member further including a lower interior cylindrical surface in snug contact with the exterior cylindrical surface of said stator, and second means for retaining said stator in stationary position and snug contact with said lower cylindrical surface, said upper and lower surface being coaxial with each other to substantially precisely center the rotor within the stator, wherein said first means includes a first step formed between the upper surface and lower surface, said first step defining an upwardly directed stop surface disposed in a common plane generally perpendicular to the longitudinal axis of said member to receive the lower end of the pivot housing in nesting engagement.

* * * * *